United States Patent [19]

Kimball et al.

[11] 4,316,895

[45] Feb. 23, 1982

[54] ENDORPHINS HAVING PLACENTAL OR PANCREATIC ORIGIN

[76] Inventors: Charles D. Kimball, The Highlands, Seattle, Wash. 98177; John C. Houch, 420 28th Pl., Seattle, Wash. 98199

[21] Appl. No.: 109,233

[22] Filed: Jan. 3, 1980

[51] Int. Cl.³ .................. A61K 37/00; C07G 7/00; C07C 103/52; A61K 37/02
[52] U.S. Cl. .................. 424/177; 260/112 R; 260/112.5 R
[58] Field of Search .................. 424/177; 260/112.5 R, 260/112 R

[56] References Cited

U.S. PATENT DOCUMENTS

| | | | |
|---|---|---|---|
| 3,842,063 | 10/1974 | Chance et al. | 424/177 |
| 4,038,222 | 7/1977 | Li | 424/177 |
| 4,073,885 | 2/1978 | Pert et al. | 424/177 |
| 4,098,778 | 7/1978 | Li | 424/177 |
| 4,105,651 | 8/1978 | Hughes | 424/177 |
| 4,116,950 | 9/1978 | Li | 424/177 |

OTHER PUBLICATIONS

Science vol. 207, 1980, pp. 78–80.
Chem. Abstr. vol. 90, 1979, p. 36766b.
Biol. Abstr. vol. 68, p. 27799.
Biol. Abstr. 67, p. 59719.
Biol. Abstr. 69, p. 22555.

*Primary Examiner*—Delbert R. Phillips
*Attorney, Agent, or Firm*—David G. Conlin; George W. Neuner

[57] ABSTRACT

A peptide endorphin having a molecular weight in the range of about 4500 to 5000 daltons is described. This peptide endorphin has $\beta$-endorphin-like activity, reacting immunologically to rabbit antisera prepared against $\beta$-endorphin and displacing Naloxone from opiate receptors in brain tissue. Unlike $\beta$-endorphin, however, this peptide endorphin does not exhibit respiratory depressor effect when administered to mice. This peptide endorphin can be obtained from placental and pancreatic tissue, preferably by extracting with dilute mineral acid.

7 Claims, 4 Drawing Figures

ENDORPHINS HAVING PLACENTAL OR PANCREATIC ORIGIN

FIELD OF THE INVENTION

This invention is related to endorphins such as β-endorphin and enkephalin and particularly to an endorphin having a molecular weight in the range of about 4500 to 5000 daltons, i.e., equivalent to a peptide comprising about 43 amino acid residues, having β-endorphin-like activity, and which can be obtained from tissues of the placenta and the pancreas, as well as method of making and using such endorphins.

BACKGROUND OF THE INVENTION

Beta endorphin is an endogenous opioid peptide hormone released from the pituitary during stress having the same peptide sequence as the 61 to 91 portion of beta lipotropin. This peptide has been recognized as an endogenous morphine-like analgesic.

Gautray et al., Am. J. Obst. Gynecol., 129, 211 (1977) disclosed that amnionic fluid contains a significant amount of beta endorphin as detected by radioimmunoassay (RIA). Further, acid extracts of human placenta have been disclosed by Nakai et al., Life Sci., 23, 2013 (1978) to contain both β-endorphin and ACTH as well as beta lipotropin.

SUMMARY OF THE INVENTION

We have discovered an endorphin peptide (hereafter p-endorphin) having a molecular weight in the range of about 4500 to 5000 datrons (i.e., equivalent to a peptide comprising about 43 amino acid residues) that has β-endorphin-like activity in- radioimmunoassay against β-endorphin rabbit antisera and in radioreceptor assay (RRA) against H$^3$-Naloxone in brain tissue. The p-endorphin also exhibits an analgesic effect in mammals. Unlike β-endorphin, our endorphin peptide does not exhibit respiratory depressor effect when administered to mice.

P-endorphin, in accord with the present invention can be found in substantial quantities in or associated with placental and pancreatic tissue although it is apparently absent in a number of other tissues including, for example, liver, lung, kidney, spleen and thymus. Preferably, the p-endorphin is extracted from tissue preparations by dilute mineral acid. The extract is then clarified, neutralized and incubated at 70° C. to denature proteolytic enzymes. The resulting product is then further purified by ultra filtration.

The p-endorphin of this invention is useful among other things for the therapeutic treatment of mental depression, opium and alcohol addiction, and geriatric dysphoria.

DESCRIPTION OF THE INVENTION

Figure 1:
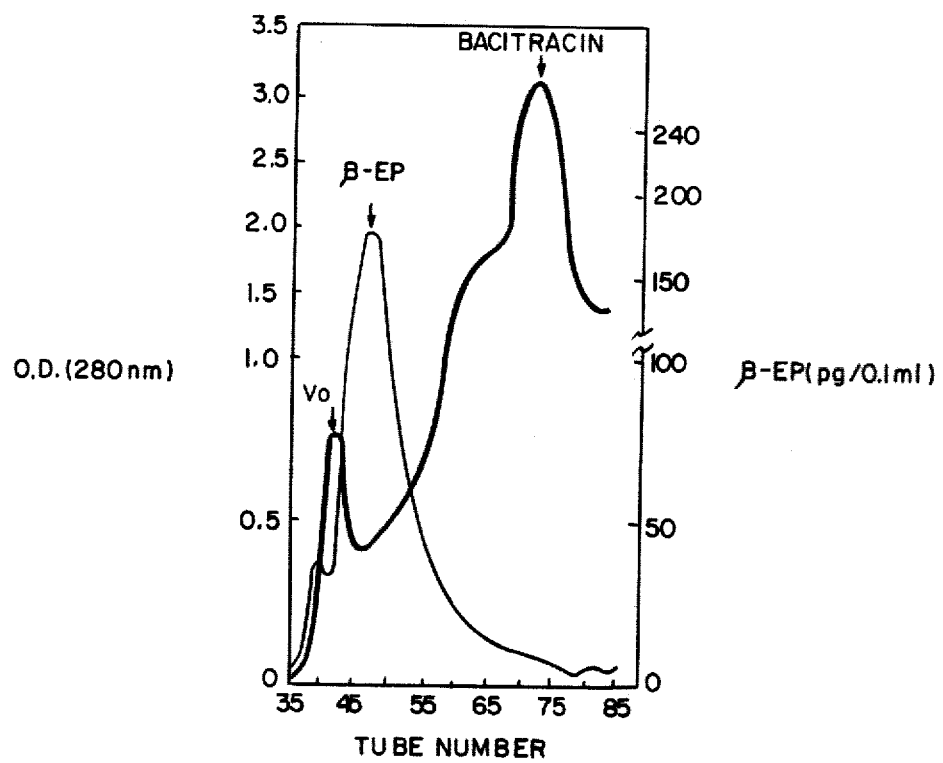
FIG. 1 is an illustration of the elution profile of a p-endorphin preparation prepared from placental tissue in accord with an embodiment of this invention.

In accord with the present invention p-endorphin preparations are prepared by extraction from placental and pancreatic tissue with dilute mineral acid. Placental tissue is preferably extracted directly with dilute mineral acid, for example 0.1 M HCl with a pH of 1.8. Because extracts of fresh bovine and porcine pancreas apparently do not contain p-endorphin when extracted by dilute mineral acid, it is preferred to prepare such pancreatic tissue by treating it with large volumes of acetone to form a powder. This acetone powder is then extracted with dilute mineral acid as above. Also found useful for extracting p-endorphin are commercial dessicated and defatted tissue powders prepared from pancreas by Viobin Corporation (Monticello, IL) including "Pancrelipase" which is similar extract of pork pancreas prepared using 1, 2-dichloroethanol.

Because p-endorphin is a peptide subject to proteolysis, it is preferable to extract it with dilute mineral acid. The extract is clarified by centrifugation, quickly neutralized and incubated, for example at 70° C. for 20 minutes, to denature both peptidases and proteases.

The resulting clarified supernatant can be further purified by, for example, hollow-fiber ultrafiltration and concentrated.

The β-endorphin-like activity of p-endorphin molecules has been demonstrated utilizing and RIA test kit for β-endorphin developed by the New England Nuclear Company, involving antisera from rabbits prepared against synthetic human beta endorphin synthesized by the Peptide Division of the Beckman Company, and utilizing an RRA involving the displacement of H$^3$-Naloxone from binding sites in the brain after extensive washing to eliminate contaminating peptidases. A crude placental extract in accord with this invention required 4.4 mg/ml to displace 50% H$^3$-Naloxone in the RRA.

The extracts of p-endorphin were also subjected to molecular exclusion chromatography. As a result it was concluded that the molecular weight of p-endorphin is in the range of about 4500 to 5000 daltons, i.e., approximately 4800 daltons and that this is equivalent to a peptide that comprises about 43 amino acid residues. Thus, the p-endorphin of our invention has a substantially higher molecular weight than the pituitary hormone. This difference can be attributed to about 12 extra amino acid residues, as aforesaid, or to about two carbohydrate residues.

The following examples are set forth to further illustrate the present invention. In the examples the following assays are used. 1. Radioimmunoassay (RIA) Procedure The New England Nuclear Company has devised a RIA test kit for beta endorphin using antisera prepared in the rabbit against synthetic human beta endorphin. The procedures described in the instruction book involve removal of the free $^{125}$I-labeled synthetic beta endorphin antigen from that bound to the antibody with activated charcoal. This method is sensitive to a minimum of 2 picograms/ml of beta endorphin and is unreactive to both ACTH and enkephalin. The method has shown some cross-reactivity with beta lipotropin, however. Recovery experiments indicate approximately 80 to 85% recovery of synthetic beta endorphin from human plasma and we have found the normal circulating value in humans to be between 0 and 90 picograms/ml with an average of approximately 26 picograms. Internal standard deviation of replicate determinations would be approximately 11% of this mean value.

2. Radioreceptor assay (RRA) Procedure

Binding of $H^3$-Naloxone (14.6 Ci/mole, New England Nuclear) was assayed in rat brain tissue in the absence of sodium ion. Fresh rat brain with the cerebellus removed was weighed and then homogenized in 40 ml ice cold Tris HCl buffer (0.05 M,pH 7.4). After centrifugation at 48,000×g for 10 min the pellet was re-suspended in 40 ml Tris buffer and the washing procedure repeated twice. The thrice washed pellet was finally re-homogenized in 9 volumes of Tris buffer. Aliquots of the tissue brei (final assay concentration 10 mg wet weight per ml), $H^3$-Naloxone (1.2 nM) and drugs or tissue extracts were incubated in Tris buffer (2 ml) for 2 hours at 0° C. in an ice water bath. The binding reaction was terminated by filtration through Watman GF/B filters which were rinsed four times with 5 ml ice-cold buffer. Radioactivity was extracted from the filters overnight in 6 ml scintillation fluor (prepared by mixing 2 l of Toluene with 1 l Triton X100 and 16 grams Omnifluor) and measured in a liquid scintillation counter. Control displacement curves for Naltrexone and Levorphanol were determined in each individual assay. Specific $H^3$-Naloxone binding was defined as the total binding in the absence of drugs minus the binding in the presence of 1 μM Naltrexone or Levorphanol.

The binding of $H^3$-Naloxone to opiate receptors in rat brain homogenates was shown in these studies to be stereospecific as Levorphanol was 500 times more potent in displacing Naloxone than its biologically inactive enantiomer Dextrophan.

EXAMPLE 1

P-endorphin from Human Placenta

Human placenta was extracted with dilute mineral acid (0.1 M HCl, pH 1.8). This extract was clarified by centrifugation, quickly neutralized and incubated at 70° C. for 20 minutes to denature proteolytic enzymes including both peptidases and proteases. We have separately shown that human placenta contains cathepsin D protease activity, maximally active at ph 3 and completely inhibited by pepstatin. The resulting clarified supernatent in turn was expressed through a 5,000 dalton hollow-fiber Amicon ultrafilter and concentrated over a 1,000 (UM-2) membrane filter. The retentate was assayed by RIA as well as by RRA and then lyophilized. The salt-free preparation was then redissolved in elution buffer and subjected to molecular exclusion chromatography using Sephadex G-25. Of the total reactive material in three extracts each of three separate placenta, approximately 60% of the RIA activity passed through the 5,000 dalton ultrafilter. Of the 40 percent of RIA and RRA active material that did not pass through this filter, the vast majority (i.e. 85%) was found by Sephadex G-200 exclusion chromatography to be in a general weight range of between 25,000 and 50,000 daltons.

The elution profile from the G-25 chromotography is illustrated in FIG. 1 in which RIA activity is compared with the 280 nm absorbance of the column eluate and the elution volume of both $^{125}$I-labelled synthetic pituitary endorphin (3400 daltons) and bacitracin (1411 daltons) used as molecular size standards. The $^{125}$I-endorphin was also run on a G-25 column after being mixed with crude placental extract. The elution volume was the same as that demonstrated by pure standard.

The acid extract of the human placenta which passed through a 5,000 dalton ultrafilter, was chromatographed on a 2.5×90 cm column in 10 mM sodium acetate buffer pH 4.3 and 0.15 M NaCl. The absorbance at 280 nm (solid line, left ordinate) is compared with the immunoreactivity determined by RIA (shaded areas, right ordinate). The exclusion volume ($V_o$) was determined with bovine serum albumin (68,000 daltons) and the column standardized in addition by using bacitracin (1411) and by $^{125}$I-labeled synthetic human beta endorphin (3465).

The data of FIG. 1 indicate that approximately 75% of the RIA reactive p-endorphin is found in the void or exclusion volume of G-25. This is significantly larger than the standard $^{125}$I-labelled beta endorphin. Twenty percent or so of the total RIA activity that could be expressed through a 5,000 dalton ultrafilter was in a position between beta endorphin and bacitracin with a molecular weight of approximately 2200 daltons. This corresponds to gamma endorphin in size but gamma endorphin, which is released from beta endorphin by the proteolytic activity of cathepsin D and has the same sequence as the first 17 amino acids of beta endorphin, does not cross-react with beta endorphin antisera. Thus it may be that this is a fragment of p-endorphin which unlike gamma endorphin reacts with the antisera synthetic β-endorphin.

Pools of the RIA-determined p-endorphin in the void volume, as well as the RIA-identifiable material in a molecular weight range of 2200 daltons were both tested for their ability to displace radioactive Naloxone from rate brain binding sites. These results indicated that approximately 80% of the total RIA activity that moved through the 5,000 dalton filter was in the void volume and approximately 20% was held back behind standard beta endorphin. This distribution and size were unaffected whether the columns were run at pH 7.5 or at 4.5. The elution profile of this material was also developed on a BIO-RAD P6 column which has an exclusion limit of 6,000 daltons. The results indicate that this RIA determined p-endorphin having beta endorphin-like activity was held back on the P6 column but behind the void volume; i.e., it has a molecular weight of slightly less than 5,000 daltons.

Thus, by both RRA and RIA we have found that mineral acid extracts of human placenta contained two beta endorphin-like materials, most of which consisted of p-endorphin which has a molecular weight equivalent to approximately 12 more amino acids than the material characteristically extracted from the pituitary, i.e., β-endorphin. The nature of the smaller molecular weight material (2200 daltons) is unclear, since despite its size it is unlikely to be immunologically gamma endorphin. It may represent a degradation product by various peptidases of the larger molecular weight precursor which still possesses both RRA and RIA activity despite its relatively small size. Clearly, human placenta contains two endorphin peptides which differ markedly in their size from the classical pituitary-derived hormone.

EXAMPLE 2

P-endorphin from Bovine Pancreas

Acetone powders were prepared using 5 volumes of 100% acetone per gram of fresh wet weight tissue of minced calf pancreas. These powders were prepared at 4° C. and were washed twice so that the powder resulting was a constant dry weight.

Fifty grams of these acetone powders were extracted with 10 volumes of 0.1 M HCl in a Waring blender and allowed to extract with stirring at 4° C. for approximately 30 minutes. After centrifugation in the cold at 15,000×G, the clear supernatant (pH 1.8) was collected, quickly neutralized to approximately pH 7 with 0.5 N Tris-base, centrifuged, and the supernatant heated in a 90° water bath to 70° C. for 20 minutes. No precipitate resulted during this process. The clear solution was then concentrated and dialyzed on an Amicon Diaflo 500 dalton ultrafilter (UM-05) and lyophilized.

The reconstituted material (1% w/v) was subjected to hollow fiber ultrafiltration using the 5,000 dalton Amicon Diaflo system (DC-2). The material which was retained above 5,000 daltons was lyophilized. The material which passed through the 5,000 dalton hollow fiber ultrafilter was concentrated and dialyzed over UM-05 ultrafilters. The larger molecular weight material was then subjected to molecular exclusion chromatography using G-200 Sephadex with 0.1 M Tris buffer (pH 7.5). The material which passed through the filter was subjected to molecular exclusion chromatography using G-25 Sephadex at pH 4.3 (0.01 M acetate buffer) in 0.15 M NaCl. The G-200 Sephadex column was standardized with bovine serum albumin (68,000), ovalbumin (43,000) and chymotrypsinogen (25,700). The G-25 was standardized by $^{125}$I-labeled beta endorphin (Beckman Peptide) both separately in buffer and mixed with the ultrafiltrated pancreatic extract, as well as with bacitracin (1415). The elution profile from these Sephadex columns as monitored at 280 nm in the usual fashion and fractions collect in 5 ml volumes. Every fourth or fifth tube was monitored by RIA assay.

Finally, a Bio-Rad P6 column for exclusion chromatography was also prepared. Elution profiles were determined in 0.1 M Tris buffer, pH 7.5. Unlike G-25 which has an exclusion volume of approximately 5,000 D, Bio-Rad P6 has an exclusion volume of about 6,000 D.

Approximately half of this RRA and RIA-determined endorphin activity would pass through the 5,000 dalton hollow fiber ultrafilter. Material which did not pass through the filter was concentrated by further ultrafiltration, lyophilized and subjected to G-200 Sephadex exclusion chromatography. The results of screening the eluted fractions from this column by RIA are compared with the elution profiles of standard protein in FIG. 2.

Figure 2:
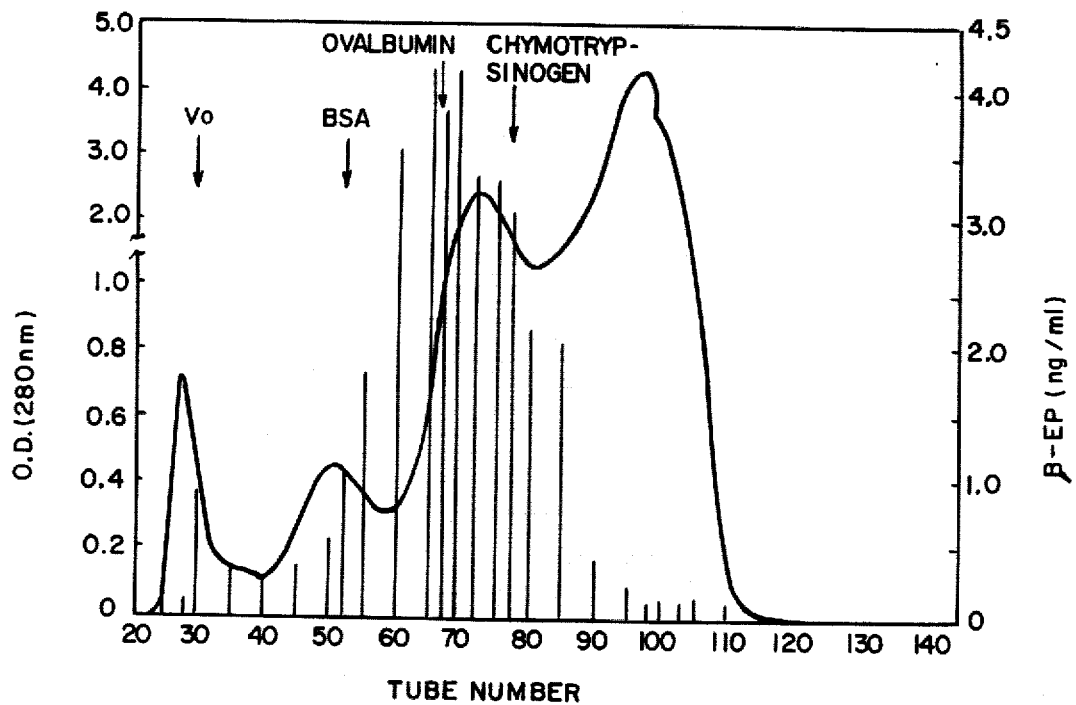
FIG. 2 is an illustration of the Sephadex G-200 elution profile and RIA β-endorphin activity profile of a p-endorphin preparation prepared from pancreatic tissue in accord with an embodiment of this invention.

FIG. 2. illustrates the Sephadex G-200 elution profile and the RIA β-endorphin activity profile. The materials that do not pass through a 5,000 dalton ultrafilter (384 mg/15 ml) were chromatographed on a 2.5×90 cm column and eluted with 0.1 M Tris-HCl buffer (pH 7.5) containing 0.02% sodium azide. The 280 nm absorbance (solid curved line, left ordinate) is compared with the RIA screening (straight lines, right ordinate) for beta endorphin immunoreactivity. Exclusion volume ($V_o$) was determined using blue Dextran 2000, and bovine serum albumin (BSA, 68,000), ovalbumin (43,000) and chymotrypsinogen (25,700) were used to standardize the column.

Approximately 80 to 85% of all the activity by RIA was found in a molecular weight range approximately between 25,000 and 50,000 daltons. Very little RIA-determinable activity was found in the molecular weight range of normal pituitary beta-lipotropin (i.e. 10,000 daltons).

Figure 3:
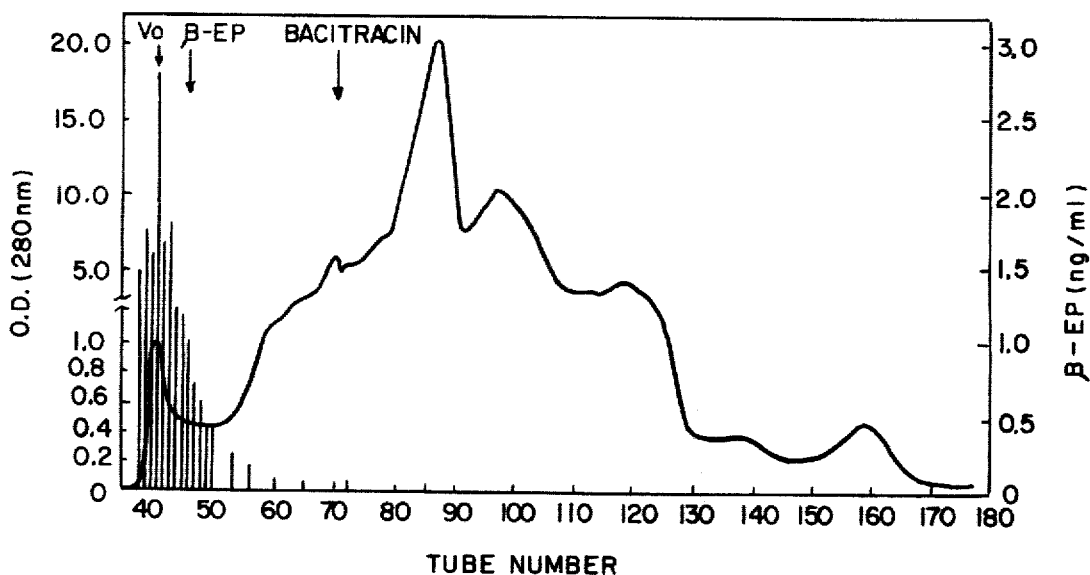
FIG. 3 is an illustration of the Sephadex G-25 elution profile and β-endorphin immunoreactive profile of pancreatic extract having molecules with a molecular weight less than 5,000 daltons.

The material having β-endorphin-like activity which passed through 5,000 daltons was then subjected to G-25 Sephadex exclusion chromatography and the results are presented in FIG. 3.

FIG. 3 illustrates the Sephadex G-25 elution profile (280 nm, solid line, left ordinate) and β-endorphin immunoreactive profile (straight line, right ordinate) of pancreatic extracts less than 5,000 daltons. 760 mg/10 ml was chromatographed on 2.5×90 cm column, eluted with 10 mM sodium acetate buffer (pH 4.3) containing 0.15 M NaCl. Exclusion volume was measured with bovine serum albumin (5,000 and up) and the column standards were bacitracin (1411) and radioactive human synthetic beta endorphin (3465) labeled with $^{125}$I. The position of elution of this labeled standard was not altered when mixed with pancreatic ultrafiltrate itself.

In FIG. 3, a comparison between the RIA screened elution profile and the UV-absorbing elution profile of p-endorphin is compared with that demonstrated for $^{125}$I-labeled synthetic beta endorphin, either in buffer solution or mixed with the tissue extract itself. In either case, its elution volume was unchanged and was distinctly less than that demonstrated by the "beta-endorphin-like" material which had passed through a 5,000 dalton hollow-fiber ultrafilter, and yet was still excluded on G-25 (exclusion volume is 5,000 daltons). None of the RIA determined p-endorphin from pancreas was found to be eluted from the column where the $^{125}$I-labeled synthetic pituitary endorphin was found.

Figure 4:
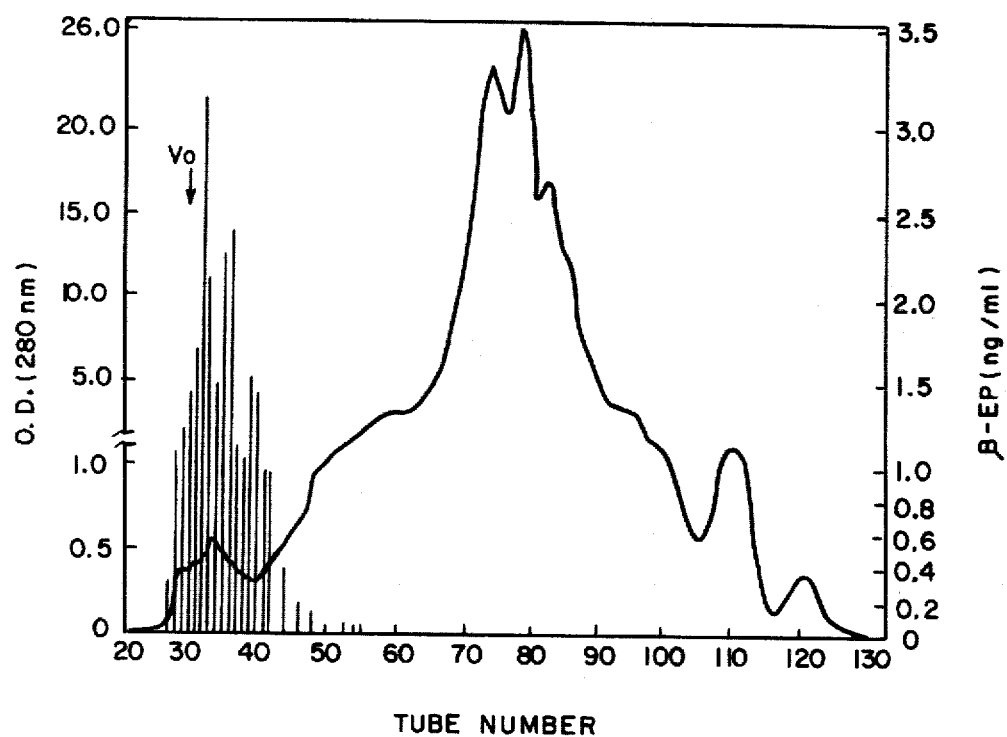
FIG. 4 is an illustration of the Bio-Gel P6 elution profile and the RIA β-endorphin activity profile of pancreatic extract having molecules with a molecular weight less than 5,000 daltons.

The void volume from G-25 was pooled, concentrated by ultrafiltration over a 500 dalton ultrafilter and subjected to exclusion chromatography using Bio-Rad P6. As shown in FIG. 4, the RIA determined p-endorphin polypeptide was held 15 ml behind the void volume of this exclusion column.

FIG. 4 illustrates the elution profile of Bio-Gel P6 elution profile and the RIA of β-endorphin profile.

Pancreatic extract of less than 5000 daltons (803 mg/10 ml) was chromatographed on a 2.5×90 cm column and eluted with 0.1 M Tris-HCl buffer, pH 7.5 in 0.02% sodium azide. 5.3 ml fractions were collected. Exclusion volume ($V_o$) was marked by bovine serum albumin. β-endorphin crossreactivity (straight lines) is expressed as ng/ml equivalents of RIA (left ordinate). Absorbance at 280 nm is the right ordinate.

The exclusion limit of P6 is approximately 6,000 daltons. Thus, it would appear that the p-endorphin having beta endorphin-like activity from acid extracts of pancreas acetone powders has a molecular weight slightly less than 5,000 daltons both by its movement through an ultafilter and by its elution pattern from G-25 and separately from P6.

Because approximately $10^{-8}$ M solutions of purified p-endorphin lead to a 50% displacement of the $H^3$-Naloxone, we calculate that by RRA approximately 50 times more material, or 2.5 μg can be found per gram of acetone powder. This extreme difference between RIA and RRA for tissue-extracted beta endorphin activity was also found in placenta. Using the RRA assay, no other tissue extracts demonstrated any significant amounts of beta endorphin-like activity except those prepared from either placenta or pancreas.

The p-endorphin of this invention also has analgesic properties as determined by the rat "tail flick" test.

Because of its opiate receptor activity and other properties, the p-endorphin of this invention can be used for the therapeutic treatment of mental depression, opium and alcoholic addiction, and geriatric dysphoria.

For each of these utilities the amount required of p-endorphin (hereafter referred to as the active ingredient) varies with the route of administration and with the severity of the condition to be treated, and ultimately is at the discretion of the physician or veterinarian. In general, however, for each of these utilities the dosage will be in the range of about 1.0 µg. to 0.3 mg. per kilogram body-weight of mammal, and preferably about 10 µg. to 0.1 mg./kg., (all dosages calculated with reference to the peptide base).

The active ingredients may be administered by any route appropriate to the condition to be treated, suitable routes including oral and parenteral (including subcutaneous, intramuscular and intravenous). It will be appreciated that the preferred route will vary with the condition to be treated.

While it is possible for the active ingredient to be administered as the raw chemical it is preferable to present it as a pharmaceutical formulation preparation.

The formulations, both veterinary and for human use, of the present invention comprise an active ingredient, as above defined, together with one or more acceptable carriers therefor and optionally other therapeutic ingredients. The carrier(s) must be "acceptable" in the sense of being compatible with the other ingredients of the formulation and not deleterious to the recipient thereof. Desirably the formulation should not include oxidizing agents and other substances with which peptides are known to be incompatible. The formulations include those suitable for oral or parenteral (including subcutaneous, intramuscular and intravenous) administration, although the most suitable route in any given case will depend upon for example, the active ingredient and the condition to be treated. The formulations may conveniently be presented in unit dosage form and may be prepared by any of the methods well known in the art of pharmacy. All methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product into the desired formulation.

Formulations of the present invention suitable for oral administration may be presented as discrete units such as capsules, cachets or tablets each containing a predetermined amount of the active ingredient; as a powder or granules; or as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine, the active ingredient in a free-flowing form such as a powder or granules, optionally mixed with a binder, lubricant, inert diluent, lubricating, surface active or dispersing agent. Moulded tablets may be made by moulding in a suitable machine, a mixture of the powdered compound moistened with an inert liquid diluent.

Formulations suitable for parenteral administration conveniently comprise sterile aqueous solutions of the active ingredient which solutions are preferably isotonic with the blood of the recipient. Such formulations may be conveniently prepared by dissolving solid active ingredient in water to produce an aqueous solution, and rendering said solution sterile may be presented in unit—or in multi-dose containers, for example sealed ampoules or vials.

It should be understood that in addition to the aforementioned ingredients the formulations of this invention may include one or more additional ingredients such as diluents, buffers, flavouring agents, binders, surface active agents, thickeners, lubricants, preservative (including anti-oxidants) and the like.

Where the formulation, for human or for veterinary use, is presented in unit dosage form, for example those unit dosage forms specifically mentioned above, each unit thereof conveniently contains the active ingredient (as above defined) in an amount in the range of about 0.5 to about 0.10 mg (all weights calculated with reference to the peptide base).

We claim:

1. An endorphin peptide composition comprising p-endorphin prepared from placental or defatted pancreatic tissue by extracting said tissue with dilute mineral acid, neutralizing the extract, incubating the neutalized extract at a temperature and for a time sufficient to denature proteolytic enzymes, and purifying the extract by treating it to exclude compounds that are too large to pass through a 5000 dalton hollow tube ultrafilter and chromatographing the portion of the extract that passes through the ultrafiler to separate the portion that cross-reacts with beta endorphin antisera and has opiate receptor activity, thus obtaining the endorphin peptide composition comprising p-endorphin having a molecular weight greater than beta endorphin.

2. The endorphin peptide composition of claim 1 wherein said extracting step is accomplished with hydrochloric acid.

3. The endorphin peptide composition of claim 1 wherein said extracting step comprises treating human placental tissue with hydrochloric acid.

4. The endorphin peptide composition of claim 1 wherein said pancreatic tissue is first treated with acetone or 1,2-dichloroethane.

5. The endorphin peptide composition of claim 1 wherein said incubating is carried out at about 70° C.

6. The endorphin peptide composition of claim 1 wherein the chromatographing step comprises separating the portion that cross-reacts with beta endorphin antisera, has opiate receptor activity, and has a molecular weight between beta endorphin and bacitracin.

7. A pharmaceutical preparation useful for therapeutic treatment of mental depression, opium addiction, alcoholic addiction and geriatric disphoria said preparation comprising effective amount of the endorphin peptide of claim 1 in a pharmacological carrier.

* * * * *